United States Patent
Curiel et al.

(10) Patent No.: US 6,210,946 B1
(45) Date of Patent: Apr. 3, 2001

(54) MODIFIED ADENOVIRUS CONTAINING A FIBER REPLACEMENT PROTEIN

(75) Inventors: David T. Curiel; Victor N. Krasnykh, both of Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/250,580

(22) Filed: Feb. 16, 1999

Related U.S. Application Data

(60) Provisional application No. 60/074,844, filed on Feb. 17, 1998, now abandoned.

(51) Int. Cl.[7] ............................ C12N 15/00; C12N 15/09; C12N 15/63; C12N 15/70; C12N 15/74
(52) U.S. Cl. ...................... 435/235.1; 435/320.1; 435/325; 435/455; 435/456; 424/93.2
(58) Field of Search .......................... 435/320.1, 325, 435/235.1, 455, 456; 514/44; 424/93.2

(56) References Cited

U.S. PATENT DOCUMENTS

| | | | |
|---|---|---|---|
| 5,770,442 | | 6/1998 | Wickham ........................... 435/320.1 |
| 5,846,782 | * | 12/1998 | Wickham et al. .................... 435/697 |
| 5,877,011 | * | 3/1999 | Armentano et al. .............. 435/320.1 |
| 5,885,808 | | 3/1999 | Spooner ............................... 435/455 |
| 6,057,155 | * | 5/2000 | Wickham et al. .................... 435/325 |

OTHER PUBLICATIONS

Eck et al. Goodman & Gilman's The Pharmacological Basis of Therapeutics, 9th Edition, Chapter 5, Gene–Based Therapy, 1996.*

Verma et al. Gene Therapy–Promises, Problems, and Prospects. Nature, vol. 389, pp. 239–242, Sep. 18, 1997.*

Gall et al. Adenovirus Type 5 and 7 Capsid Chimera: Fiber Replacement Alters Receptor Tropism without Affecting Primary Immune Neutralization Epitopes. Journal of Virology, vol. 70, No. 4, pp. 2116–2123, Apr. 1996.*

* cited by examiner

*Primary Examiner*—Deborah J. R. Clark
*Assistant Examiner*—Eleanor Sorbello
(74) *Attorney, Agent, or Firm*—Benjamin Aaron Adler

(57) ABSTRACT

The present invention provides means to modify the tropism of recombinant adenoviral vectors using genetic methods to alter the adenoviral fiber cell-binding protein while maintaining the native trimeric protein biosynthesis profile. The present invention further provides means to specifically target particular cell types for infection with recombinant adenoviral vectors using genetic methods to alter the adenoviral fiber cell-binding protein.

4 Claims, 2 Drawing Sheets

SEQUENCE LISTING

<160> NUMBER OF SEQ ID NOS: 4

<210> SEQ ID NO 1
<211> LENGTH: 40
<212> TYPE: DNA
<213> ORGANISM: artificial sequence
<220> FEATURE:
<221> NAME/KEY: primer_bind
<223> OTHER INFORMATION: Forward primer F1 used to amplify segment of
      the T4 fibritin gene encoding amino acids Ser-229 through
      the carboxy terminal Ala-487.

<400> SEQUENCE: 1
gggaacttga cctcacagaa cgtttatagt cgtttaaatg                40

<210> SEQ ID NO 2
<211> LENGTH: 37
<212> TYPE: DNA
<213> ORGANISM: artificial sequence
<220> FEATURE:
<221> NAME/KEY: primer_bind
<223> OTHER INFORMATION: Reverse primer R1 used to amplify segment of
      the T4 fibritin gene encoding amino acids Ser-229 through
      the carboxy terminal Ala-487.

<400> SEQUENCE: 2
aggccatggc caatttttgc cggcgataaa aaggtag                   37

<210> SEQ ID NO 3
<211> LENGTH: 36
<212> TYPE: DNA
<213> ORGANISM: artificial sequence
<220> FEATURE:
<221> NAME/KEY: primer_bind
<223> OTHER INFORMATION: Forward primer F2 used to amplify the

```
            5'-terminal segment of the fiber-fibritin gene assembled in
            pNEB.PK.FFBB.

<400> SEQUENCE: 3
cccctcatga agcgcgcaag accgtctgaa gatacc                                    36

<210> SEQ ID NO 4
<211> LENGTH: 42
<212> TYPE: DNA
<213> ORGANISM: artificial sequence
<220> FEATURE:
<221> NAME/KEY: primer_bind
<223> OTHER INFORMATION: Reverse primer R2 used to amplify the
            5'-terminal segment of the fiber-fibritin gene assembled in
            pNEB.PK.FFBB.

<400> SEQUENCE: 4
ccccggatcc tgccggcgat aaaaaggtag aaagcaatac cc                             42
```

MODIFIED ADENOVIRUS CONTAINING A FIBER REPLACEMENT PROTEIN

CROSS-REFERENCE TO RELATED APPLICATIONS

This application claims benefit of U.S. provisional application Ser. No. 60/074,844 filed Feb. 17, 1998, now abandoned.

FEDERAL FUNDING LEGEND

This invention was supported in part using federal funds from the National Institutes of Health. Accordingly, the Federal Government has certain rights in this invention.

BACKGROUND OF THE INVENTION

1. Field of the Invention

The present invention relates generally to the fields of vector biology and gene therapy. More specifically, the present invention relates to the production of recombinant adenoviral vectors with replacement of fibers for cell-specific targeting with concomitant elimination of endogenous tropism.

2. Description of the Related Art

Adenovirus interacts with eukaryotic cells by virtue of specific receptor recognition of domains in the knob portion of the fiber protein (21-23) which protrude from each of the twelve vertices of the icosahedral capsid. Recombinant adenovirus vectors are used in a number of gene therapy applications (21, 35, 38). This fact has derived principally from the high levels of gene transfer achievable with this vector approach both in vitro and in vivo.

Recombinant adenovirus vectors are distinguished from other systems by their unique ability to accomplish in situ gene delivery to differentiated target cells in a variety of organ contexts (5, 6, 9, 10, 12, 20, 25, 27, 29, 31). This has allowed the utilization of recombinant adenoviral vectors as an approach to treat inherited genetic diseases, such as cystic fibrosis, whereby the delivered vector may be contained within the target organ (4-13). In addition, the ability of the adenoviral vector to accomplish in situ tumor transduction has allowed the development of a variety of anti-cancer gene therapy approaches for loco-regional disease (14-18).

Adenoviral vectors can accomplish in vivo gene delivery to a variety of organs after intravenous injection. In these instances, gene transfer frequencies have been sufficiently high to correct inherited metabolic abnormalities in various murine models. Thus, adenoviral vectors fulfill two requirements of an intravenously administered vector for gene therapy: systemic stability and the ability to accomplish long-term gene expression following high efficiency transduction of muscle cells.

Adenoviruses suffer, however, from the disadvantage that the widespread distribution of the adenovirus cellular receptor precludes the targeting of specific cell types. This lack of tropism of adenoviral vectors would result in a decrease in the efficiency of transduction, as the number of virus particles available for delivery to the target cells would be decreased by sequestration by nontarget cells. Furthermore, this would allow ectopic expression of the delivered gene, with unknown and possibly deleterious consequences. Therefore, a means must be developed to redirect the tropism of the adenovirus vector specifically to target cells and permit gene delivery only to affected organs.

To this end, several groups have reported genetic modifications to the knob domain of adenovirus fiber protein and incorporation of such chimeric fibers into virion. For instance, Stevenson et al. (35) and others (24) reported successful generation of Ad5 virions containing fibers consisting of the tail and shaft domains of Ad5 fiber and the knob domain of Ad3, respectively. In addition, Michael et al. (30) demonstrated the incorporation of the gastrin-releasing peptide into the carboxy terminus of recombinant Ad5 fiber. This finding was extended by Legrand et al. (30a) who achieved rescue of recombinant adenovirus vectors containing such fibers. Wickham et al. (41) described the generation of recombinant virus containing fibers with carboxy-terminal polylysine sequences. These studies have established key feasibility issues with respect to this genetic approach but have also demonstrated a number of limiting factors, including the size of the ligand, which may disrupt the correct folding of the fiber protein.

The prior art remains deficient in the lack of effective means to produce recombinant adenoviral vectors with combination of novel targeting and ablation of native tropism. The present invention fulfills this longstanding need and desire in the art.

SUMMARY OF THE INVENTION

The present invention describes the next generation of recombinant, cell-specific adenoviral vectors. More particularly, the instant specification discloses that there are two aspects to consider in the modification of adenoviral tropism: (1) ablation of endogenous tropism; and (2) introduction of novel tropism. To expand the utility of recombinant adenoviruses for gene therapy applications, methods to alter native vector tropism to achieve cell-specific transduction are necessary. To achieve such targeting, one can incorporate ligands into the adenoviral fiber protein, which mediates primary binding of adenovirus to its cell surface receptor. As described herein, the present invention discloses the development of a targeted adenovirus created by replacement of the adenovirus fiber protein. The present invention discloses recombinant adenovirus vectors comprising fiber replacement or substitution proteins composed of the fiber tail domain, a portion of the fibritin gene from the bacteriophage T4 and a ligand domain. The recombinant adenoviral vector may also encode a therapeutic gene i.e. the herpes simplex virus thymidine kinase gene, in the presence of ganclicovir, the adenovirus is able to mediate the specific killing of cells which express the targeted receptor. The present invention thus represents the demonstration of the retargeting of a recombinant adenoviral vector via a non-adenoviral cellular receptor.

In one embodiment of the present invention, there is provided a recombinant adenovirus vector lacking endogenous viral tropism but having novel tropism, wherein the adenovirus vector is modified to produce a replacement adenoviral fiber protein so as to modify viral tropism, wherein the replaced fiber gene comprises the amino-terminal portion of the adenoviral fiber gene including the tail domain, the carboxy-terminal portion of the T4 bacteriophage fibritin gene and a ligand, wherein the replaced adenovirus fiber retains its ability to trimerize and retains its native biosynthesis profile, wherein the ligand is selected from the group consisting of physiological ligands, anti-receptor antibodies and cell-specific peptides, wherein the adenoviral vector further contains a therapeutic gene, wherein said therapeutic gene is the herpes simplex virus-thymidine kinase gene.

In another embodiment of the present invention, there is provided a method of killing tumor cells in an individual in need of such treatment, comprising the steps of pretreating said individual with an effective amount of the recombinant adenoviral vector and administering ganciclovir to said individual.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
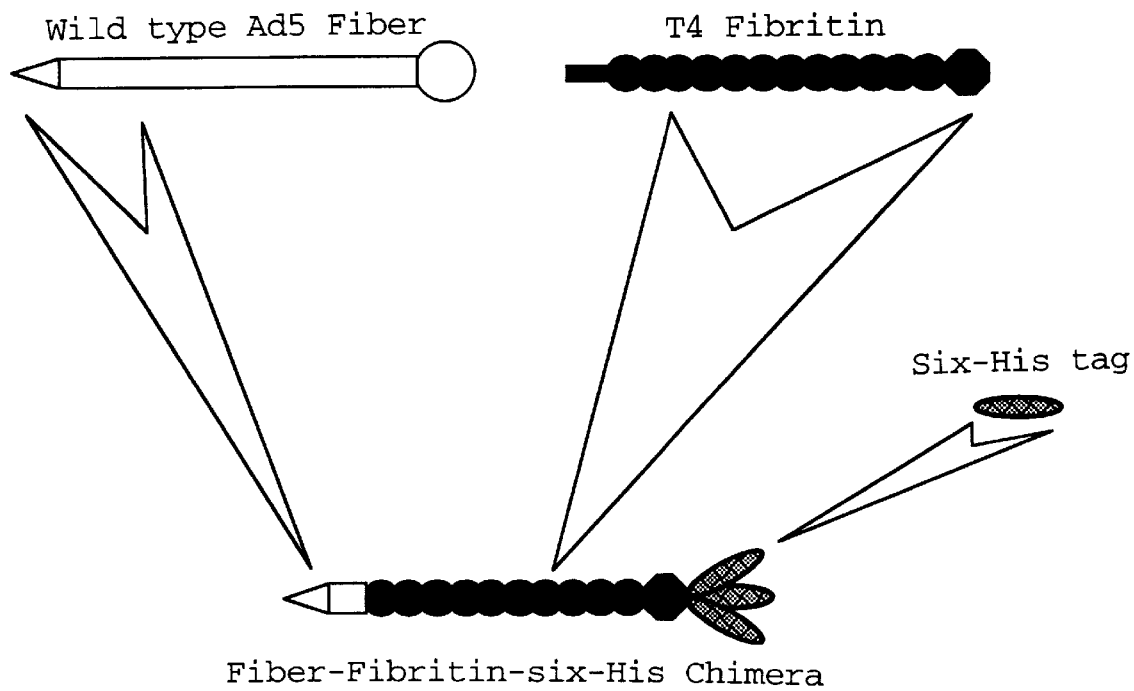
FIG. 1 shows the schema of the substitute fiber consisting of a fiber-fibritin-six-histidine chimera.

The present invention is directed to an adenovirus, wherein the adenovirus is modified by replacing the adenovirus fiber protein with a fiber replacement protein. In a preferred embodiment, the fiber replacement protein comprises: a) an amino-terminal portion comprising an adenoviral fiber tail domain; b) a chimeric fiber replacement protein; and c) a carboxy-terminal portion comprising a targeting ligand.

The following description will allow a person having ordinary skill in this art to determine whether a putative fiber replacement protein would function as is desired in the compositions and methods of the present invention. Generally, the fiber replacement protein associates with the penton base of the adenovirus. Structurally, the fiber replacement protein is preferably a rod-like, trimeric protein. It is desirable for the diameter of the rod-like, trimeric protein to be comparable to the native fiber protein of wild type adenovirus. It is important that the fiber replacement protein retain trimerism when a sequence encoding a targeting ligand is incorporated into the carboxy-terminus. In a preferred aspect, a representative example of a fiber replacement protein is T4 bacteriophage fibritin protein. More generally, the fiber replacement protein can be selected from the group consisting of trimeric structural proteins, trimeric viral proteins and trimeric transcription factors. Other representative examples of fiber replacement proteins include isoleucine trimerization motif and neck region peptide from human lung surfactant D. Preferably, the fiber replacement protein has a coiled coil secondary structure. The secondary structure provides stability because of multiple interchain interactions.

The fiber replacement protein does not have to be a natural protein. In fact, a person having ordinary skill in this art would be able to construct an artificial protein. Preferably, such an artificial fiber replacement protein would have a coiled coil secondary structure.

In the adenovirus of the present invention, the targeting ligand is selected from the group consisting of physiological ligands, anti-receptor antibodies, cell-specific peptides and single chain antibodies. In one embodiment, the adenovirus carries in its genome a therapeutic gene. A representative example of a therapeutic gene is a herpes simplex virus thymidine kinase gene.

The present invention is also directed to a method of killing tumor cells in an individual in need of such treatment, comprising the steps of: pretreating said individual with an effective amount of the adenovirus of the present invention; and administering ganciclovir to said individual.

Previous results obtained by modifying the Ad5 fiber suggest that the trimeric structure of the native fiber protein is not stable enough to accomodate long inserts and that the molecule will not tolerate the incorporation of large ligands. The knob seems to be the major (or only) structural component of the fiber maintaining the fibers trimeric structure, while the rest of the molecule "passively" follows the trimerization process initiated by the knob. In order to create a recombinant virion lacking endogenous fiber tropism and possessing a novel tropism, one could "split" the functions of the adenoviral fiber which is normally performed by the knob domain between two different protein moieties which would replace the knob. This could be achieved by replacing the knob with an external trimerization motif to maintain the trimerization of the knobless fiber, and simultaneous introduction into the fiber of a ligand capable of targeting the virion to a novel receptor.

Since the role of the fiber is presumably to place the cell-binding site away from the surface of the virion, the fiber may be replaced with another rod-like trimeric protein. In addition to being trimeric, the protein should have the ability to associate with the penton base of adenovirus and be incorporated into the virion. To prevent problems of incompatibility, the amino-terminus of the chimeric protein can be incorporated into the the tail domain of the adenovirus fiber. Furthermore, the putative fiber replacement protein should tolerate the incorporation of (relatively) large additional sequences corresponding to targeting ligands into its carboxy terminus.

Fibritin, of bacteriophage T4, is the protein which forms the "collar" and the "whiskers" of the phage particle and meets many of the criteria discussed above. The 486 amino acid sequence of fibritin consists of an amino-terminal domain (47 residues), a large central domain and a carboxy-terminal domain (29 residues). The central domain has 12 segments of various length, each having an α-helical coiled-coil structure. Extensive biophysical and sequence analysis has modeled fibritin as a parallel triple-stranded α-helical coiled-coil. Trimers of fibritin are stable at temperatures up to 65° C. Significantly, both fibritin lacking residues at the amino terminus and recombinant fibritins containing amino-terminal extensions assemble correctly into trimers. The carboxy-terminal domain of fibritin is necessary for trimerization and carboxy-terminal fusions of fibritin with the Ad5 fiber knob form stable trimers. In addition, when overexpressed in E.coli, recombinant fibritin and its derivatives are soluble. Another feature of fibritin that makes it an attractive candidate for fiber replacement is the fact that it is flexible. Therefore, the length requirements established by the nature of the fiber can easily be met by fibritin, similar to the flexible fibers of bovine Ad3 and CELO virus.

Definitions

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specific gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use for the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence to hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. Prokaryotic hosts may include *E. coli, S. tymphimurium, Serratia marcescens* and *Bacillus subtilis*. Eukaryotic hosts include yeasts such as *Pichia pastoris*, mammalian cells and insect cells and plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

In addition, the invention may includes portions or fragments of the fiber or fibritin genes. As used herein, "fragment" or "portion" as applied to a gene or a polypeptide, will ordinarily be at least 10 residues, more typically at least 20 residues, and preferably at least 30 (e.g., 50) residues in length, but less than the entire, intact sequence. Fragments of these genes can be generated by methods known to those skilled in the art, e.g., by restriction digestion of naturally occurring or recombinant fiber or fibritin genes, by recombinant DNA techniques using a vector that encodes a defined fragment of the fiber or fibritin gene, or by chemical synthesis.

As used herein, "chimera" or "chimeric" refers to a single transcription unit possessing multiple components, often but not necessarily from different organisms. As used herein, "chimeric" is used to refer to tandemly arranged coding sequence (in this case, that which usually codes for the adenovirus fiber gene) that have been genetically engineered to result in a protein possessing region corresponding to the functions or activities of the individual coding sequences.

The "native biosynthesis profile" of the chimeric fiber protein as used herein is defined as exhibiting correct trimerization, proper association with the adenovirus capsid, ability of the ligand to bind its target, etc. The ability of a candidate chimeric fiber-fibritin-ligand protein fragment to exhibit the "native biosynthesis profile" can be assessed by methods described herein.

A standard Northern blot assay can be used to ascertain the relative amounts of mRNA in a cell or tissue in accordance with conventional Northern hybridization techniques known to those persons of ordinary skill in the art. Alternatively, a standard Southern blot assay may be used to confirm the presence and the copy number of the gene of interest in accordance with conventional Southern hybridization techniques known to those of ordinary skill in the art. Both the Northern blot and Southern blot use a hybridization probe, e.g. radiolabelled cDNA or oligonucleotide of at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the terms "fiber gene" and "fiber" refer to the gene encoding the adenovirus fiber protein. As used herein, "chimeric fiber protein" refers to a modified fiber gene as defined above.

As used herein the term "physiologic ligand" refers to a ligand for a cell surface receptor.

The present invention is directed to a vector system that provides both a highly efficient and specific targeting of adenovirus vector for the purpose of in vivo gene delivery to predefined cell types after administration. In the recombinant adenoviral vector of the present invention, a fiber replacement protein comprising a fiber-fibritin-ligand is employed to target adenoviral vector to a specific cell for gene therapy. This is accomplished by the construction of adenoviral vectors which contain fiber-fibritin-ligand chimeras. These adenoviral vectors are capable of delivering gene products with high efficiency and specificity to cells expressing receptors which recognize the ligand component of the fiber-fibritin-ligand chimera. A person having ordinary skill in this art would recognize that one may exploit a wide variety of genes encoding e.g. receptor ligands or antibody fragments which specifically recognize cell surface proteins unique to a particular cell type to be targeted.

A "fiber replacement protein" is a protein that substitutes for fiber and provide 3 essential feature: trimerizes like fiber, lacks adenoviral tropism and has novel tropism.

The following examples are given for the purpose of illustrating various embodiments of the invention and are not meant to limit the present invention in any fashion.

EXAMPLE 1

Experimental Design

To demonstrate that fibritin can be used to replace the fiber in recombinant AdS virions, the following experimental strategy was employed. First, a chimeric fiber-fibritin gene encoding fiber tail, the first and the second motifs of the fiber shaft domain, as well as the fiber knob domain fused with a segment of fibritin protein, was designed. In this construct, the fibritin coding sequence replaced most of the fiber shaft coding sequence. The chimeric protein encoded by this recombinant gene will therefore resemble the Ad5 fiber protein in which almost all of the shaft domain has been replaced with the fibritin.

EXAMPLE 2

Construction of a Recombinant Adenovirus Vector Containing a Fiber-fibritin Protein In order to facilitate the subsequent transfer of the newly designed fiber gene into the Ad5 genome, the gene has been assembled in a previously made fiber shuttle vector pNEB.PK.RGD-4C. For this, pNEB.PK.RGD-4C was digested with NaeI and NcoI to delete most of the fiber shaft coding sequence starting from Gly-76 through His-363. This vector was then used to clone a segment of the T4 fibritin gene encoding amino acids Ser-229 through the carboxy terminal Ala-487. The segment of the fibritin gene was PCR amplified using primers F1 (5' GGG AAC TTG ACC TCA CAG AAC GTT TAT AGT CGT TTA AAT G 3') (SEQ ID No. 1) and R1(5' AGG CCA TGG CCA ATT TTT GCC GGC GAT AAA AAG GTA G 3') (SEQ ID No. 2). In addition to the fibritin sequence, the PCR product also contained four codons at the 5' end corresponding to the fiber Gly-79 through Thr-82, whereas at the 3' end, three codons corresponding to Lys-360 through Gly-362 of the fiber were added. Thus, the PCR-generated DNA fragment was digested with NcoI and ligated with the NaeI-NcoI-digested pNEB.PK.RGD-4C, resulting in pNEB.PK.FF$_{BB}$.

The gene assembled in PNEB.PK.FF$_{BB}$ encodes the amino-terminal portion of the fiber protein including the complete tail domain, the first and second (and a small portion of the third) repeat of the shaft, as well as the last 222 carboxy-terminal amino acids of the fiber. The carboxy-terminal amino acids includes the entire knob, most of repeat 20 and repeats 22 and 21. The amino-terminal and carboxy-terminal portions of the fiber protein are connected by the carboxy-terminal segment of fibritin, starting from Ser-229 of the fibritin open reading frame.

In order to generate a recombinant adenovirus genome containing the fiber-fibritin gene, the plasmid PNEB.PK-.FF$_{BB}$ was used for homologous recombination with pVK50, producing pVK510. To recover the virus of interest, pVK510 was digested with PacI and used to transfect 293 cells. The newly generated virus, Ad5FF$_{BB}$, contains the fiber-fibritin protein. The generation of this virus has demonstrated that the amino-terminal portion of the fiber protein genetically fused with the fibritin sequence can efficiently associate with the Ad5 penton base, thereby allowing formation of mature virions.

EXAMPLE 3

Construction of a Recombinant Adenovirus Vector Containing a Knobless Fiber-fibritin Protein In order to prove the ability of the fibritin molecule to maintain the trimeric structure of the entire fiber-fibritin chimera in the absence of the knob, the 3' terminal portion of the chimera was replaced with a short sequence encoding a two amino acid residue linker and a 6-His tag (FIG. 1). The newly generated gene was used to direct the expression of the knobless fiber-fibritin in *E. coli*. First, the 5'-terminal segment of the fiber-fibritin gene previously assembled in PNEB.PK.FF$_{BB}$ (encoding the fibritin sequence fused with the fiber tail and the beginning of the shaft) was PCR amplified using primers F2 (5' CCC CTC ATG AAG CGC GCA AGA CCG TCT GAA GAT ACC 3') (SEQ ID No. 3) and R2 (5' CCC CGG ATC CTG CCG GCG ATA AAA AGG TAG AAA GCA ATA CCC 3') (SEQ ID No. 4), digested with BspHI and BamHI and cloned into the bacterial expression vector pQE60 which had been digested with NcoI and BamHI, thereby generating PQE.FF$_{BB}$.

EXAMPLE 4

Figure 2:
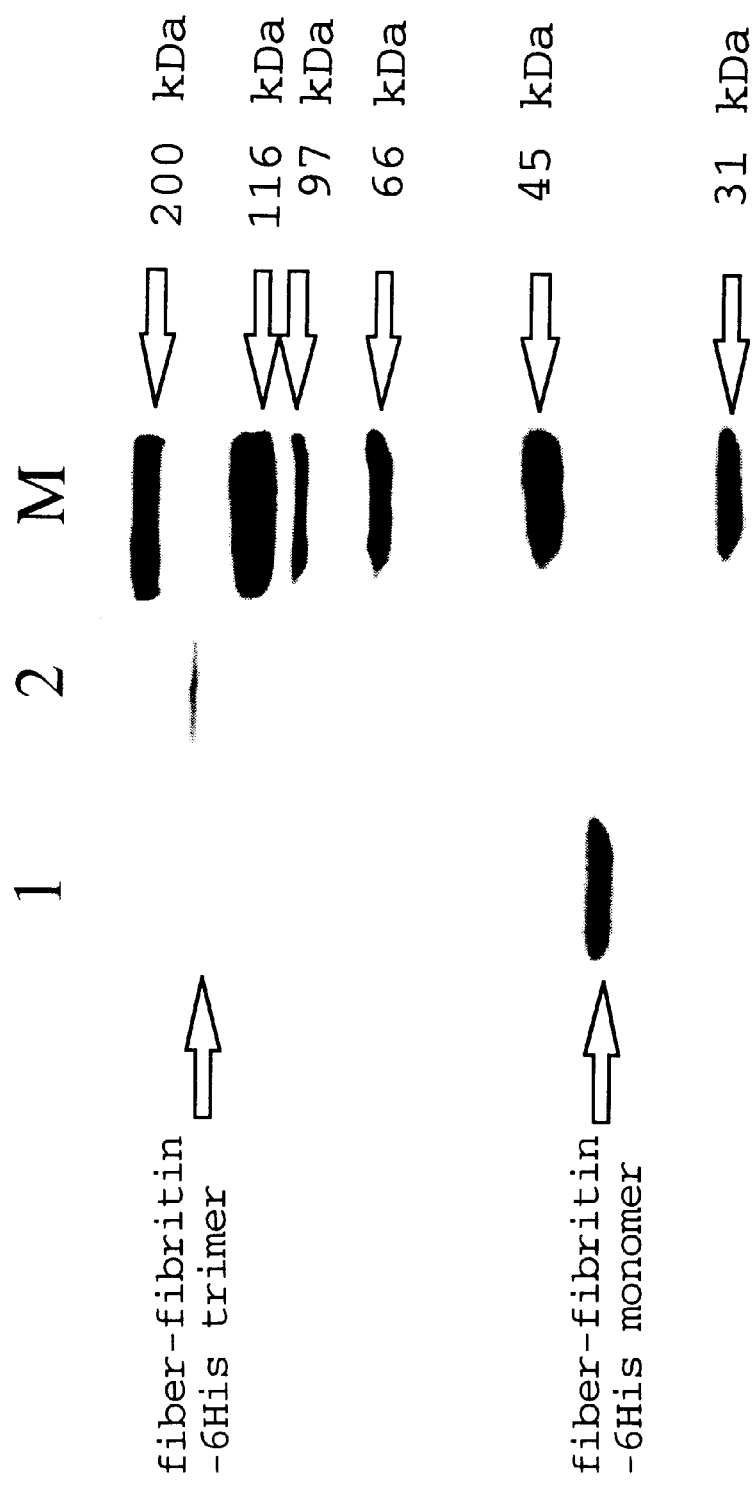
FIG. 2 shows a SDS gel electrophoresis of the fiber-fibritin-6histidine chimeric protein expressed in E. coli. Proteins were separated on 4–10% SDS-PAA gels and then stained with Coomassie briliant blue. Lane 1, fiber-fibritin-6His denatured by boiling; Lane 2, fiber-fibritin-6His native trimer; Lane 3, protein molecular mass standards.

Efficacy of the Recombinant Adenovirus Containing the Knobless Fiber-fibritin Chimera As a result of the cloning described above, a recombinant adenovirus containing a modified fiber gene encoding the fiber-fibritin-6His chimera has been obtained. To confirm the trimeric structure of this protein, the virion was purified using Ni-NTA-agarose from *E. coli* cells harboring pQE.FF$_{BB}$, and then analysed by SDS-polyacrylamide gel electrophoresis. This analysis demonstrated that, indeed, the fiber-fibritin chimera is a trimeric protein (FIG. 2), therefore, strongly supporting the idea of utilization of the fibritin protein for trimerization of knobless fibers. These results were supported by Western blot analyses of the chimeric protein utilizing anti-6-His tag monoclonal antibody tetra-His and anti-fiber monoclonal 4D2 which recognizes an epitope localized within the tail domain of the fiber molecule: both monoclonal antibodies identified the bands seen on the Coomassie-stained gel as fiber-fibritin-six-His chimera (data not shown).

Significantly, the fact that the fiber-fibritin chimera containing the carboxy-terminal 6-His tag efficiently bound to Ni-NTA-agarose indicates that the 6-His tag was available for binding in the context of the fiber-fibritin chimera. These results demonstrate that replacement of this tag with a targeted ligand results in an efficient interaction between a recombinant adenovirus carrying a chimeric fiber-fibritin-ligand and a ligand-specific cellular receptor.

As is well known by those having ordinary skill in this art, the fiber replacement protein will allow the incorporation of various targeting motifs e.g., targeting ligands, targeting antibodies The following references were cited herein:
1. Jolly, D., in *Cancer Gene Therapy*, eds. Appleton & Lange, pp. 51–64, (1994).
2. Trapnell, B. C., et al., *Current Opinion in Biotechnology* 5:617–625, (1994).
3. Siegfried *Exp Clin Endocrinol* 101:7–11, (1993).
4. Bout, A., et al., *Human Gene Therapy* 5:3–10, (1994).
5. La Salle, G. L. G., et al., *Science* 259:988–990, (1993).
6. Csete, M. E., et al., *Transplantation Proceedings* 26(2) :756–757, (1994).
7. Maeda, H., et al., *Gastroenterology* 106:1638–1644, (1994).
8. Jaffe, H. A., et al., *Nature Genetics* 1:372–378, (1992).
9. DeMatteo, R. P., et al., *Annals Of Surgery* 222(3) :229–242, (1995).
10. Mastrangeli, A., et al., *Am J Physiol* 266:G1146–G1155, (1994).
11. Moullier, P., et al., *Kidney International* 45:1220–1225, (1994).
12. Mitani, K., et al., *Human Gene Therapy* 5:941–948, (1994).
13. Crystal, R. G., et al., *Nature Genetics* 8:42–51, (1994).
14. Clayman, G. L., et al., *Cancer Gene Therapy* 2(2) :105–11, (1995).
15. Liu, T.-J., et al., *Cancer Research* 54:3662–3667, (1994).
16. Smythe, W. R., et al., *Ann Thorac Surg* 57:1395–1401, (1994).
17. Fujiwara, T., et al., *Cancer Reearch* 54:2287–2291, (1994).
18. Addison, C. L., et al., *Proc Natl Acad Sci* 92:8522–8526, (1995).
19. Strattford-Perricaudet, et al., *J Clin Invest* 90:626–630, (1992).
20. Huard, J., et al., *Gene Therapy* 2:107–115, (1995).
21. Henry, L. J., et al., *Journal of Virology* 68:5239–5246, (1994).
22. Stevenson, S. C., et al., *J. of Virology* 69:2850–2857, (1995).
23. Louis, N., et al., *Journal of Virology* 68:4104–4106, (1994).
24. Michael, S. I., et al., *Gene Therapy* (1995).

Any patents or publications mentioned in this specification are indicative of the levels of those skilled in the art to which the invention pertains. These patents an publications are herein incorporate by reference to the same extent as if each individual publication was specifically an individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, an specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed:

1. An adenovirus modified by replacing the adenovirus fiber protein with a fiber replacement protein so that said adenovirus does not bind to coxsacki-adenovirus receptor, wherein said fiber replacement protein comprises:
   a) an amino-terminal portion comprising an adenoviral fiber tail domain that associates with the penton base protein;
   b) a chimeric fiber replacement protein that provides the trimerization function, said fiber replacement protein is T4 bacteriophage fibritin protein; and
   c) a carboxy-terminal portion comprising a targeting ligand.

2. The adenovirus of claim 1, wherein the fiber replacement protein retain trimerism when a sequence encoding a targeting ligand is incorporated into the carboxy-terminus.

3. The adenovirus of claim 1, wherein said fiber replacement protein is soluble.

4. The adenovirus of claim 1, wherein said targeting ligand is selected from the group consisting of physiological ligands, anti-receptor antibodies, cell-specific peptides and single chain antibodies.

* * * * *